United States Patent
Chen et al.

(10) Patent No.: US 7,069,770 B2
(45) Date of Patent: Jul. 4, 2006

(54) AMMONIA SENSOR ELEMENT, HEATER, AND METHOD FOR MAKING THE SAME

(75) Inventors: David K. Chen, Rochester Hills, MI (US); Raymond L. Bloink, Swartz Creek, MI (US); Carlos A. Valdes, Flint, MI (US); Eric L. Ker, Grand Blanc, MI (US); Jinping Zhang, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/909,552

(22) Filed: Aug. 2, 2004

(65) Prior Publication Data

US 2006/0021420 A1    Feb. 2, 2006

(51) Int. Cl.
*G01N 9/00*    (2006.01)

(52) U.S. Cl. ...................... 73/31.05; 73/23.2
(58) Field of Classification Search .............. 73/31.05, 73/23.2, 23.3
See application file for complete search history.

(56) References Cited

U.S. PATENT DOCUMENTS

| | | | |
|---|---|---|---|
| 5,143,696 A | 9/1992 | Haas et al. | 422/90 |
| 5,252,292 A | 10/1993 | Hirata et al. | |
| 6,069,013 A | 5/2000 | Plog et al. | |
| 6,463,789 B1 | 10/2002 | Moos et al. | 73/31.06 |
| 6,634,210 B1* | 10/2003 | Bosch et al. | 73/23.33 |
| 6,634,212 B1* | 10/2003 | Moos et al. | 73/31.05 |
| 6,656,346 B1* | 12/2003 | Ino et al. | 208/120.01 |
| 2002/0182127 A1 | 12/2002 | Braun et al. | |
| 2004/0118703 A1* | 6/2004 | Wang et al. | 205/780.5 |

FOREIGN PATENT DOCUMENTS

| | | |
|---|---|---|
| EP | 0709670 A1 | 5/1996 |
| WO | WO 01/40783 A2 | 6/2001 |

\* cited by examiner

*Primary Examiner*—Daniel S. Larkin
(74) *Attorney, Agent, or Firm*—Paul L. Marshall

(57) ABSTRACT

A sensor element can comprise a co-fired heater section, a sensing section, and a third insulating layer disposed between the electrode portion and the temperature sensor. The heater section can comprise a heater, a shield, and a temperature sensor, with a first insulating layer disposed between the heater and the shield, and a second insulating layer disposed between the shield and the temperature sensor. The sensing section can comprise an electrode portion and a sensing portion, wherein the sensing portion is disposed on a side of the electrode portion opposite the heater section.

15 Claims, 3 Drawing Sheets

$R = f(NH_3, H_2O, T)$
$C = f(NH_3, H_2O, T)$

AMMONIA SENSOR ELEMENT, HEATER, AND METHOD FOR MAKING THE SAME

BACKGROUND

Exhaust gas generated by combustion of fossil fuels in furnaces, ovens, and engines, for example, contains nitrogen oxides (NOx), unburned hydrocarbons (HC), and carbon monoxide (CO). Vehicles, e.g., diesel vehicles, utilize various pollution-control after treatment devices such as, for example, a NOx absorber or Selective Catalytic Converter (SCR), to reduce NOx. For diesel vehicles using SCR, the NOx reduction can be accomplished by using ammonia gas ($NT_3$). In order for SCR catalyst to work efficiently, and to avoid pollution breakthrough, an effective feedback control loop is needed. To develop such control technology, there is an ongoing need for economically-produced and reliable commercial ammonia sensors.

SUMMARY

Disclosed herein are ammonia sensors, heaters, and methods for making the same. In one embodiment, the sensor element can comprise a co-fired heater section, a sensing section, and a third insulating layer disposed between the electrode portion and the temperature sensor. The heater section can comprise a heater, a shield, and a temperature sensor, with a first insulating layer disposed between the heater and the shield, and a second insulating layer disposed between the shield and the temperature sensor. The sensing section can comprise an electrode portion and a sensing portion, wherein the sensing portion is disposed on a side of the electrode portion opposite the heater section.

In another embodiment, the sensor element can comprise: a heater section, a sensing section, and a third insulating layer disposed between the heater section and the sensing section. The heater section can comprise a heater, a shield, and a temperature sensor, with a first insulating layer disposed between the heater and the shield, and a second insulating layer disposed between the shield and the temperature sensor. The heater can comprise a serpentine and leads in electrical communication with the serpentine, wherein the serpentine comprises center inner legs, second inner legs, and outer legs, and wherein the second inner leg has a varying second width. The sensing section can comprise an electrode portion and a sensing portion, wherein the sensing portion is disposed on a side of the electrode portion opposite the heater section.

In one embodiment, the heater can comprise a serpentine and leads. The serpentine can comprise center inner legs, second inner legs, and outer legs, wherein the outer legs are in electrical communication with the leads. The center inner legs, second inner legs, and/or the outer legs can have a convexo-convex geometry.

In one embodiment, the method for making a sensor element can comprise disposing a shield between a heater and a temperature sensor to form a green laminate with a first insulating layer disposed between the heater and the shield, and a second insulating layer disposed between the shield and the temperature sensor. The laminate can be co-fired to form a co-fired substrate. A capacitor precursor can be printed on the temperature sensor side of the substrate. The capacitor can be patterned and a sensor portion can be disposed on a side of the capacitor opposite the substrate.

The above-described and other features will be appreciated and understood by those skilled in the art from the following detailed description, drawings, and appended claims.

BRIEF DESCRIPTION OF THE DRAWINGS

Refer now to the figures, which are meant to be exemplary, not limiting, and wherein the like elements are numbered alike.

DETAILED DESCRIPTION

It should be noted that the terms "first," "second," and the like herein do not denote any order or importance, but rather are used to distinguish one element from another, and the terms "a" and "an" herein do not denote a limitation of quantity, but rather denote the presence of at least one of the referenced items. Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.).

Figure 1:
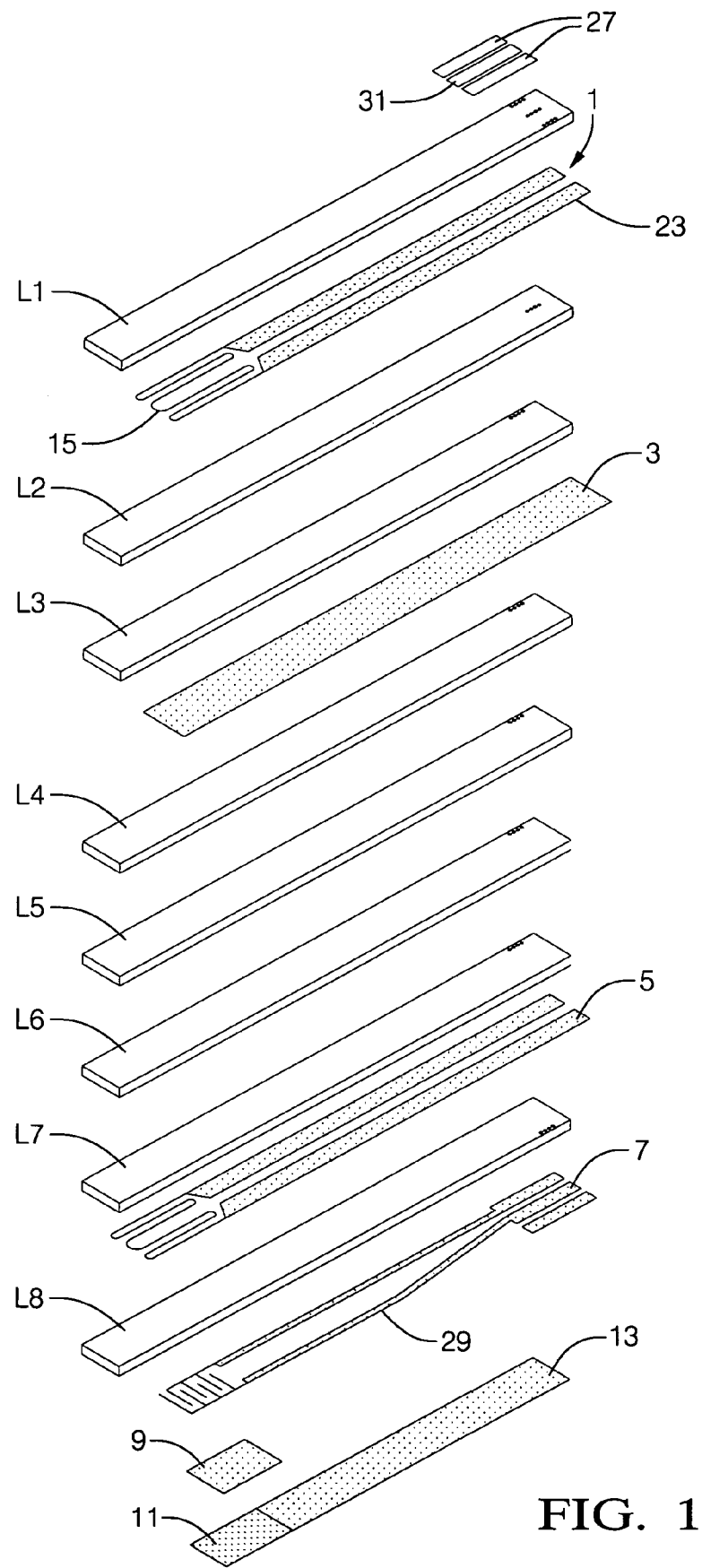
FIG. 1 is an exploded, isometric view of an exemplary ammonia sensor element.
Figure 2:
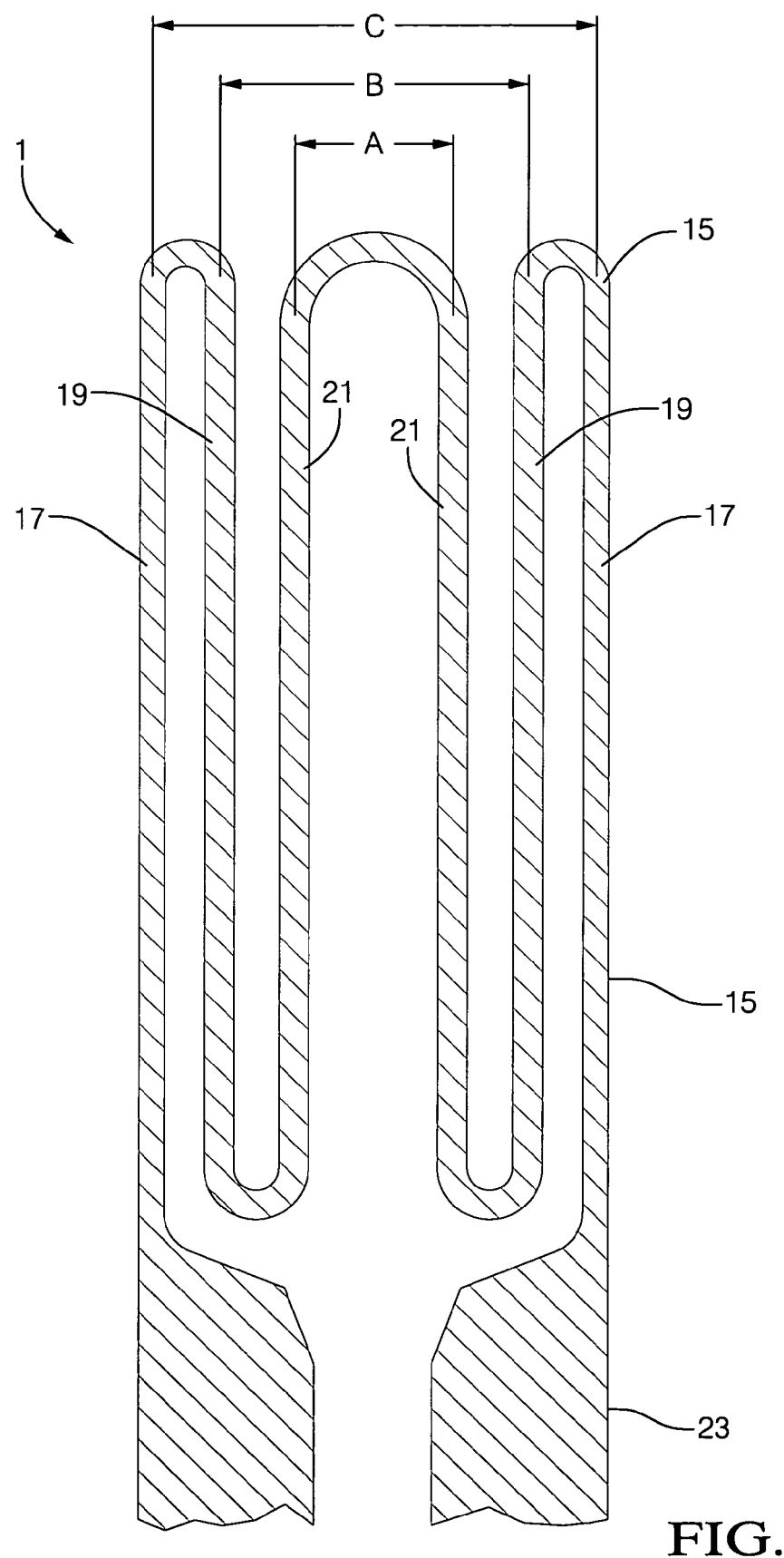
FIG. 2 is a partial, planar view of an exemplary heater.

The ammonia sensor element comprises a sensing section and a co-fired heater section. The co-fired heater section comprises a heater (e.g., a ceramic heater), a shield, and a temperature sensor, while the sensing section comprises an ammonia sensing material. FIGS. 1 and 2 illustrate an exemplary ammonia sensor element. The heater section comprises heater 1 (comprising a heater serpentine 15 and heater leads 23), insulating layers (e.g., alumina layers L1–L8), shield 3, and temperature sensor 5 (comprising a temperature element and temperature leads). The sensor section can comprise a capacitor 7 (comprising a capacitor element and capacitor leads), a protective divider 9, a sensing portion 11 at a sensor end of the ammonia sensor element, and a covering 13, with a insulating layer L8 disposed between the temperature sensor 5 and the capacitor 7.

The heater 1 can be any heater capable of maintaining the sensor end of the ammonia sensor element at a sufficient temperature to enable the sensing of ammonia. The heater 1 can comprise platinum, palladium, tungsten, molybdenum, and the like, or alloys or combinations comprising at least one of the foregoing, or any other heater compatible with the environment. The heater 1 can be printed (e.g., thick film printed) onto an alumina layer (e.g., L1 and/or L2) to a sufficient thickness to attain the desired resistance and heating capability. The heater thickness can be, for example, about 10 micrometers to about 50 micrometers, or so.

Optionally, the heater 1 can be designed to attain a substantially uniform temperature (e.g., a temperature gradient across the sensing portion 11 of less than or equal to about 5° C.). The heater 1 can have a serpentine 15 with variable width serpentine legs (outer legs 17, second inner legs 19, and center inner legs 21) and with leg separation distances between the centerlines of the legs "A", "B", "C". For example, the separation "C", between the outer legs 17, can be about 4.5 mm to about 5.5 mm; the separation "B", between the second inner legs 19, can be about 3.0 mm to about 4.0 mm; and the separation "A", between the center inner legs 21, can be about 1.5 mm to about 2.0 mm. These separation distances provide a variable spacing between different legs. Namely, the spacing between the centerlines of the two inner legs "A" can be about 1.5 mm to about 2.0 mm. The spacing between the centerlines of the center inner leg to second inner leg can be about 0.75 mm to about 1.25 mm. The spacing between the centerline of the second inner leg to the centerline of the outer leg can be about 0.65 mm to about 1.0 mm.

One or more of the serpentine legs 17, 19, 21 can vary in width. Optionally, one or more of these legs can have a convexo-convex geometry (i.e., broader in the center than at the ends). For example the center inner legs 21 can have a center width that varies from about 0.20 mm to about 0.30 mm, or, more specifically, from about 0.27 mm to about 0.34 mm. The second inner legs 19 can have a width that varies from about 0.30 mm to about 0.50 mm, or, more specifically, from about 0.35 mm to about 0.45 mm. The outer legs 17 can have a width varies from about 0.20 mm to about 0.35 mm, or, more specifically, by about 0.25 mm to about 0.32 mm. It is noted that, unless specified otherwise, all widths disclosed herein are prior to firing (i.e., in the green state).

Due to the design of the heater, namely the varying width of one or more of the legs, the heater attains a more uniform temperature distribution during operation. For example, during operation, the heater can have a longitudinal temperature gradient (i.e., a gradient measured perpendicular to the leg separation widths "A", "B", "C") of less than or equal to about 5° C., or, more specifically, less than or equal to about 3° C. The heater may also have, during operation, a latitudinal temperature gradient (i.e., a gradient measured parallel to the leg separation widths "A", "B", "C") of less than or equal to about 5° C., or, more specifically, less than or equal to about 3° C., and, even more specifically, less than or equal to about 1° C.

The shield 3 is disposed between the heater 1 and the temperature sensor 5. The shield 3 can comprise, for example, a closed layer, a line pattern (connected parallel lines, serpentine, and/or the like), and/or the like. The shield 3 can comprise any material capable of enhancing the electrical isolation of the heater from the temperature sensor. Possible shield materials include precious metal (such as platinum (Pt), palladium (Pd), gold (Au) and the like, as well as alloys and combinations comprising at least one of the foregoing materials.

The temperature sensor 5 can be any temperature sensor capable of monitoring the temperature of the sensing end of the ammonia sensor element, such as a resistance temperature detector (RTD). Potential materials for the temperature sensor 5 can be any material having a sufficient temperature coefficient of resistance to enable temperature determinations, and have a sufficient melting point to withstand the co-firing temperature (e.g., of about 1,400° C. or so). Some possible materials include those employed for the heater 1. The temperature sensor can comprise a serpentine portion with a line width of less than or equal to about 0.15 mm.

The sensing section is disposed on a side of the temperature sensor 5, opposite the heater 1. For example, the sensing section can comprise the sensing portion 11, and an electrode portion 7, and optionally the protective divider 9. The sensing portion 11 comprises zeolite. The sensor can be designed such that the impedance (e.g., complex impedance) of the sensor portion, or the derived variables, serve as the measured variable. Possible zeolites that can be used in the sensor portion include, for example, alumino-silicates of the pentasil and/or beta crystal structure, in the hydrogen form. The ratio of silica to alumina (often called the modulus of the zeolite) can vary be about 25 to about 400. One possible zeolite is an alumino-silicate pentasil with a modulus of about 80 to about 90. Additionally, the ammonia form of the alumino-silicate pentasil and/or beta crystal structure having a modulus of about 25 to about 400 can also be used. This form is converted to the hydrogen form by a heat treatment (e.g., heated to about 600° C. for a short period of time).

The electrode portion 7 can comprise various designs capable of sensing ammonia, such as an interdigitated structure, a two electrode arrangement, a four conductor arrangement, and the like. When a capacitor is employed, for example, it can resemble inter-digitating fingers (such a structure is referred to also as an interdigited capacitor (IDC)). This capacitor can comprise various materials, including gold (Au), and alloys and combinations comprising gold, such as gold-platinum alloys and gold-palladium alloys.

The capacitor can be produced in various fashions. For example, a capacitor precursor can be produced using a thick film technique (e.g., a printing technique) to form a complete (closed) or an already pre-structured capacitor layer can be employed as a precursor. Subsequent to forming the precursor, it can be fired (e.g., to densify and stabilize the gold) and then patterned as desired. The precursor can be fired at temperatures of greater than or equal to 600° C., e.g., at temperatures of about 800° C. to about 900° C. Patterning can be accomplished utilizing photolithography. A uniform layer of a photoresist material can be applied over the fired precursor, such as by a spinning method. The photoresist material can comprise a suitable photosensitive resin and a suitable solvent. A photo mask corresponding to the desired capacitor can then be disposed adjacent to the photoresist and be illuminated or irradiated by a UV source such that an area of the photoresist can be removed later by a developer. The area removed is dependent upon the type of photoresist (with a positive photoresist, the irradiated area is removed, and with negative photoresist, the non-irradiated area of the material is removed). A portion of the fired precursor (e.g., gold) can then be etched away from the areas with no photoresist covering, to form the capacitor. The residual photoresist can then be removed (e.g., stripped using a strong solvent, such as acetone).

The optional covering 13, disposed adjacent the sensing portion 11, on a side of the electrode portion 7, opposite the temperature sensor 5, protects the leads 29 of the electrode portion 7. The covering can comprise any material capable of protecting the leads 29, including alumina, spinel, glass, and the like, as well as combinations comprising at least one of the foregoing.

Optionally disposed between the electrode portion 7 and the sensing portion 11 is a protective divider 9. The protective divider 9 provides a barrier to prevent the contaminants in electrode 7 and in the heater portion from migrating to the sensing portion 11 and from degrading the performance. Possible materials for the protective divider include silicon dioxide (silica), alumina, and the like, as well as combinations comprising at least one of the foregoing materials.

Leads are disposed across various insulating layers to enable the electrical connection of external wiring to portions of the heater 1, electrode portion 7, and temperature sensor 5. The leads extend from a terminal end (i.e., the end opposite the sensing end) where they are in electrical communication, through corresponding vias (not shown), to pads (e.g., heater pads 27, ground 31, etc.). (See FIG. 1) The leads and vias comprise electrically conductive material.

The vias, disposed at or near the terminal end of the ammonia sensor element, comprise holes with electrically conductive material and provide electrical communication through the appropriate insulating layers, e.g., L1–L8.

As illustrated in FIG. 1, the one or more insulating layers can be disposed between the heater 1 and the shield 3, between the shield 3 and the temperature sensor 5, and between the temperature sensor 5 and the capacitor 7. The insulating layers L1–L8 can each be up to about 500 micrometers thick or so, depending upon the number of layers employed, or, more specifically, a thickness of about 50 micrometers to about 200 micrometers. These layers can be formed using ceramic tape casting methods or other methods for forming layers. Desirably, between the temperature sensor 5 and the electrode portion 7, a sufficiently thick insulating layer(s) can be employed to attain an overall thickness between the electrode portion 7 and the temperature sensor 5 of about 100 micrometers to about 300 micrometers. A thicker insulation layer may be achieved by using thicker green tape or using multi-layers for the insulation.

The insulating layers L1–L8 can be co-fired with the heater section. The surface roughness ($R_a$) of the layer L8, disposed adjacent to the capacitor can be less than or equal to about 0.5 micrometers, or, more specifically, less than or equal to about 0.3 micrometers, and even more specifically, less than or equal to about 0.2 micrometers.

Formation of the sensor element comprises forming the heater section, co-firing the heater section, disposing the electrode portion on the co-fired heater section, optionally disposing the protective divider over the sensing end of the electrode portion, disposing the sensing portion over the protective divider, and disposing the covering over the electrode portion leads. For example, a heater serpentine can be screen printed on to a green insulating layer, while the heater leads can be screen printed onto the same or an adjacent green insulating layer. These layers can be laid-up such that the heater leads contact the heater serpentine outer legs. A shield can be screen printed onto a side of the adjacent green layer or onto a third green layer that can be laid-up on a side of the adjacent green layer opposite the heater. A temperature sensor can be printed onto one or more green layers as with the heater. These layer(s) are laid-up on a side of the shield opposite the heater. Optionally, more green insulating layers can be laid-up between the shield and the temperature sensor. These layers can then be co-fired to form the heater section. A mixture of the electrode material with solvent and, optionally binder, can be prepared for application to the heater section. The mixture can be printed onto heater section on a side of the temperature sensor opposite the heater. The heater section can then again be fired to a sufficient temperature to densify the gold and form a precursor. Once fired, the precursor can be patterned. Optionally, a protective divider can be disposed over at least the sensing end of the electrode portion (e.g., spun on) prior to printing the sensing portion over the sensing end of the electrode portion. Optionally, a covering can be disposed over the leads of the electrode portion to form the ammonia sensor element. Each of these optional layers can be dried and fired prior to the application of another layer. To protect the ammonia sensor element, the element can be disposed in a housing to form an ammonia sensor. Although the ammonia sensor can be used in various applications, including factories and the like, it is particularly useful in vehicle exhaust systems, such as heavy duty diesel truck applications.

Ammonia sensor elements that do not employ the above described co-firing process: (1) take numerous, sequential, thick-film printing and firing steps to make the sensor element; (2) the insulating layer between the temperature sensor and the capacitor is prone to electrical leakage, which creates noise or shorts between the temperature sensor and the capacitor; (3) the insulating layer between the temperature sensor and the capacitor does not have a smooth surface for good photolithographic processing and; (4) the heater does not provide a uniform temperature (e.g., the temperature gradient can be greater than or equal to 10° C.).

The ammonia sensor element disclosed herein employs a simplified process having reduced processing time and producing a sensor having fewer defects. Fewer of the present sensors are prone to electrical leakage, and the layer between the temperature sensor and the electrode portion is not porous; i.e., the amount of poor samples (rejected sensors) prepared using the present co-firing process constituted an about 50% reduction in rejected parts compared to other processes.

Additionally, the disclosed heater enables a uniform temperature distribution that improves heating of the sensing end and operation of the sensor. Heaters with uniform thickness legs can have temperature gradients up to about 60° C. in the longitudinal direction, generally the temperature gradients are at least 10° C. to about 15° C. in the longitudinal direction. The heater with the varying width legs, and particularly with a convexo-convex geometry, attains temperature gradients in the longitudinal direction of less than or equal to about 5° C., and of less than or equal to about 3° C. in the latitudinal direction. It is noted that a reduction of the temperature gradient improves the accuracy of the ammonia measurement. Typically, reducing the gradient by 5° C. can increase the accuracy by about 20%, or more.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Figure 3:
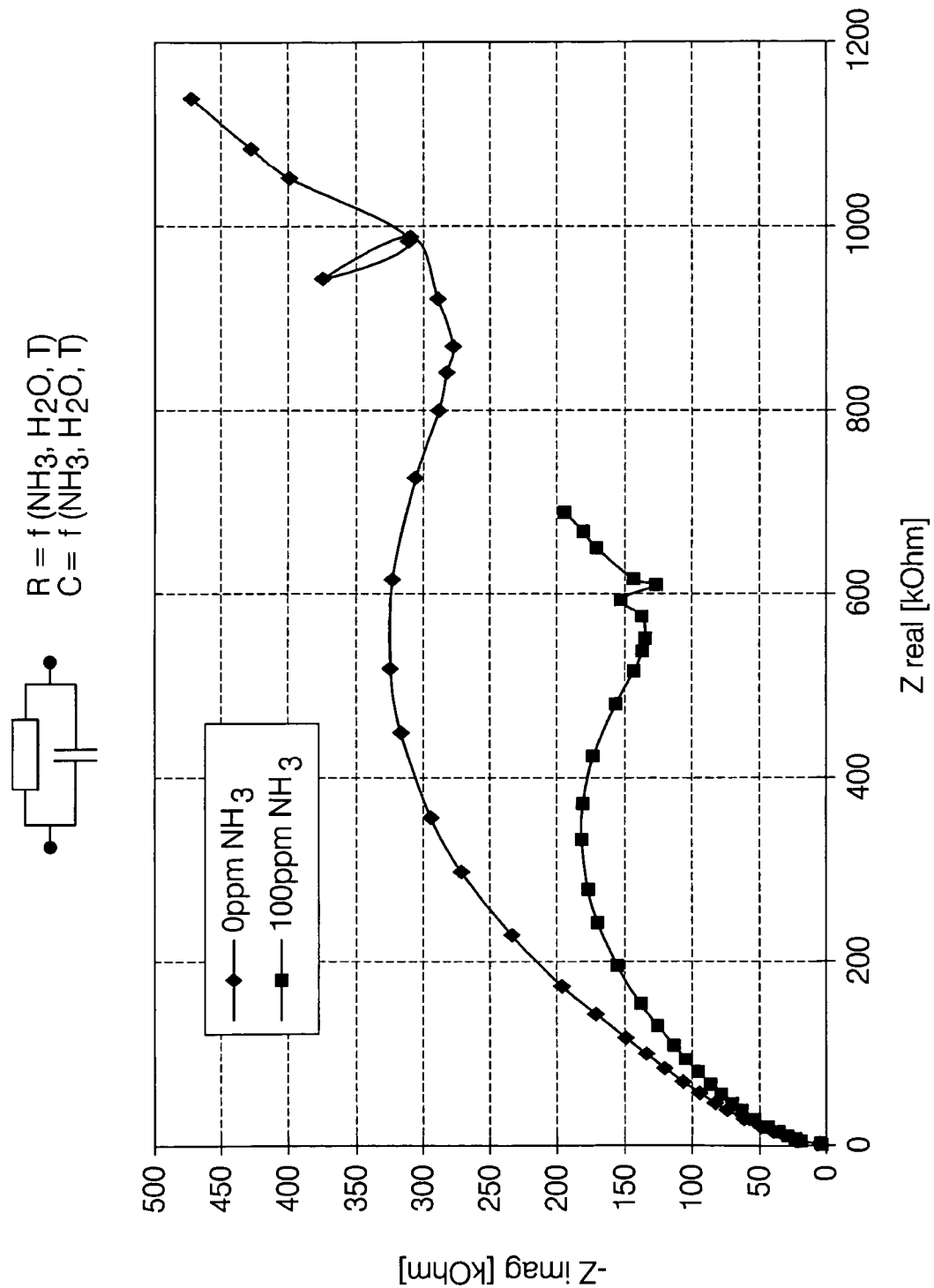
FIG. 3 is a graphical representation of an ammonia sensing model and impedance sweep for the ammonia sensor element of FIG. 1.

Referring to FIG. 3, a graphical representation of an ammonia sensing model and an impedance sweep for two embodiments of the ammonia sensor element of FIG. 1 are illustrated. Specifically, the model depicts an equivalent circuit comprising a parallel resistance and capacitance whose values (R & C) are derived as a function of ammonia content (NH3), water content (H20) and temperature (T). The graphical impedance characteristics of two models, one at 0 ppm (parts per million) and one at 100 ppm ammonia are depicted graphically with real impedance (Z) in kOhm on the ordinate and imaginary impedance (-Z) in kOhm on the abscissa of a plane Cartesian coordinate system.

The invention claimed is:

1. A sensor element, comprising:
   a co-fired heater section comprising a heater, a shield, and a temperature sensor, with a first insulating layer disposed between the heater and the shield, and a second insulating layer disposed between the shield and the temperature sensor;

a sensing section comprising an electrode portion and a sensing portion, wherein the sensing portion is disposed on a side of the electrode portion opposite the heater section; and a third insulating layer disposed between the electrode portion and the temperature sensor, wherein the heater further comprises, a serpentine, wherein the serpentine comprises center inner legs, second inner legs, and outer legs, and wherein the second inner legs have a varying second width, and leads in electrical communication with the outer legs, wherein, during operation, the heater has a longitudinal temperature gradient of less than or equal to about 5° C.

2. The sensor element of claim 1, wherein, during operation, the heater has a latitudinal temperature gradient of less than or equal to about 5° C.

3. The sensor element of claim 1, wherein the center inner legs have a center width that varies from about 0.20 mm to about 0.30 mm, prior to co-firing.

4. The sensor element of claim 1, wherein the second width varies from about 0.30 mm to about 0.50 mm, prior to co-firing.

5. The sensor element of claim 1, wherein the outer legs have an outer width that varies from about 0.20 mm to about 0.35 mm, prior to co-firing.

6. The sensor element of claim 1, wherein the second inner leg has a convexo-convex geometry, prior to co-firing.

7. The sensor element of claim 1, wherein spacing between centerlines of two center inner legs is about 1.5 mm to about 2.0 mm prior to co-firing.

8. The sensor element of claim 1, wherein spacing between a centerline of a center inner leg to a centerline of a second inner leg is about 0.75 mm to about 1.25 mm prior to co-firing.

9. The sensor element of claim 1, wherein spacing between a centerline of a second inner leg to a centerline of a outer leg is about 0.65 mm to about 1.0 mm prior to co-firing.

10. A sensor element, comprising:

a co-fired heater section comprising a heater, a shield, and a temperature sensor, with a first insulating layer disposed between the heater and the shield, and a second insulating layer disposed between the shield and the temperature sensor;

a sensing section comprising an electrode portion and a sensing portion, wherein the sensing portion is disposed on a side of the electrode portion opposite the heater section; and a third insulating layer disposed between the electrode portion and the temperature sensor, wherein the third insulating layer has a surface roughness of less than or equal to about 0.5 micrometers.

11. The sensor element of claim 10, wherein the electrode portion comprises a capacitor.

12. The sensor element of claim 1, wherein the sensing portion comprises a zeolite.

13. The sensor element of claim 12, wherein the zeolite comprises an alumino-silicate comprising a pentasil and/or beta crystal structure.

14. A sensor element, comprising:

a heater section comprising a heater, a shield, and a temperature sensor, with a first insulating layer disposed between the heater and the shield, and a second insulating layer disposed between the shield and the temperature sensor;

a sensing section comprising an electrode portion and a sensing portion, wherein the sensing portion is disposed on a side of the electrode portion opposite the heater section; and a third insulating layer disposed between the electrode portion and the temperature sensor;

wherein the heater comprises a serpentine and leads in electrical communication with the serpentine, wherein the serpentine comprises center inner legs, second inner legs, and outer legs, and wherein the second inner legs have a varying second width, and wherein the third insulating layer has a surface roughness of less than or equal to about 0.5 micrometers.

15. A sensor element, comprising:

a co-fired heater section comprising a heater, a shield, and a temperature sensor, with a first insulating layer disposed between the heater and the shield, and a second insulating layer disposed between the shield and the temperature sensor;

a sensing section comprising an electrode portion and a sensing portion, wherein the sensing portion is disposed on a side of the electrode portion opposite the heater section;

a third insulating layer disposed between the electrode portion and the temperature sensor; and a protective divider disposed between the electrode portion and the sensing portion, prior to co-firing.

* * * * *